United States Patent [19]
Weidner

[11] Patent Number: 6,087,391
[45] Date of Patent: *Jul. 11, 2000

[54] METHOD OF RENDERING ORGANIC COMPOUNDS SOLUBLE IN FATTY SYSTEMS, NOVEL CHEMICAL COMPLEXES OF SUCH COMPOUNDS AND VARIOUS APPLICATIONS OF THE COMPLEXES

[76] Inventor: Morten Sloth Weidner, Hornemansgade 40, 4.tv., DK-2100 Copenhagen Ø, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/716,444
[22] PCT Filed: Mar. 14, 1995
[86] PCT No.: PCT/DK95/00118
  § 371 Date: Sep. 16, 1996
  § 102(e) Date: Sep. 16, 1996
[87] PCT Pub. No.: WO95/25084
  PCT Pub. Date: Sep. 21, 1995

[30] Foreign Application Priority Data

Mar. 14, 1994 [DK] Denmark .................. 0296/94

[51] Int. Cl.$^7$ .................. A61K 31/355; A61K 31/07; A61K 31/12; A61K 35/78
[52] U.S. Cl. .................. 514/458; 424/58; 424/195.1; 426/606; 426/607; 554/115; 554/183; 554/185; 514/547; 514/567; 514/570; 514/648; 514/690; 514/725; 514/728; 514/734
[58] Field of Search .................. 424/58, 195.1; 426/606, 607; 554/115, 183, 185; 514/458, 547, 567, 570, 648, 690, 725, 728, 734

[56] References Cited

U.S. PATENT DOCUMENTS 4,156,719 5/1979 Sezaki et al. .................. 424/118
5,487,893 1/1996 Vachy et al. .................. 424/195.1

FOREIGN PATENT DOCUMENTS 1 601 613 11/1981 United Kingdom .
WO 92/03121 3/1992 WIPO .

OTHER PUBLICATIONS

Japanese patent 57022681, published Feb. 5, 1982 (abstract only).
Japanese patent 58208383, published Dec. 5, 1983 (abstract only).
Japanese patent 60199817, published Oct. 9, 1985 (abstract only).
Japanese patent 63174912, published Sep. 19, 1988 (abstract only).
Japanese patent 02204417, published Aug. 14, 1990 (abstract only).
Japanese patent 06113742, published Apr. 26, 1994 (abstract only).
Tesko et al., Chem. Abst. 72:131284, 1970.
Tateo et al., Chem. Abst. 110:22543, 1989.

*Primary Examiner*—Peter O'Sullivan
*Attorney, Agent, or Firm*—Darby & Darby

[57] ABSTRACT

Organic compounds containing at least one hydrophilic group are rendered soluble in fatty systems by the formation of a chemical complex with a carrier selected among fatty acid esters of polyhydric hydroxyalkanes having general formula (I)

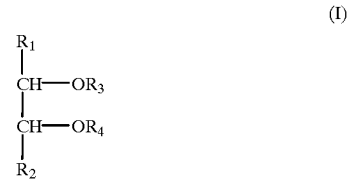

(I)

wherein $R_1$ is H or $-CH_2OR_5$, $R_2$ is H or $-CH_2OR_6$, and each of $R_3$, $R_4$, $R_5$ and $R_6$ is independently a saturated or unsaturated fatty acid moiety having 1–30 carbon atoms or a saturated fatty acid moiety having 1–3 carbon atoms, with the proviso that at least one of $R_3$, $R_4$, $R_5$ and $R_6$ is a saturated or unsaturated fatty acid moiety having 1–30 carbon atoms, R2 and at least one or, when any of $R_1$ and $R_2$ is not H, at least two of $R_3$, $R_4$, $R_5$ and $R_6$ is a saturated fatty acid moiety having 1–3 carbon atoms. Diacetates of common monoglycerides are especially preferred as the carriers for forming such complexes. The complexes are applicable for the incorporation of compounds containing hydrophilic groups into e.g. pharmaceuticals, cosmetics, foodstuffs and feeds, diet supplements and natural medicines as well as technochemical compositions.

18 Claims, 7 Drawing Sheets

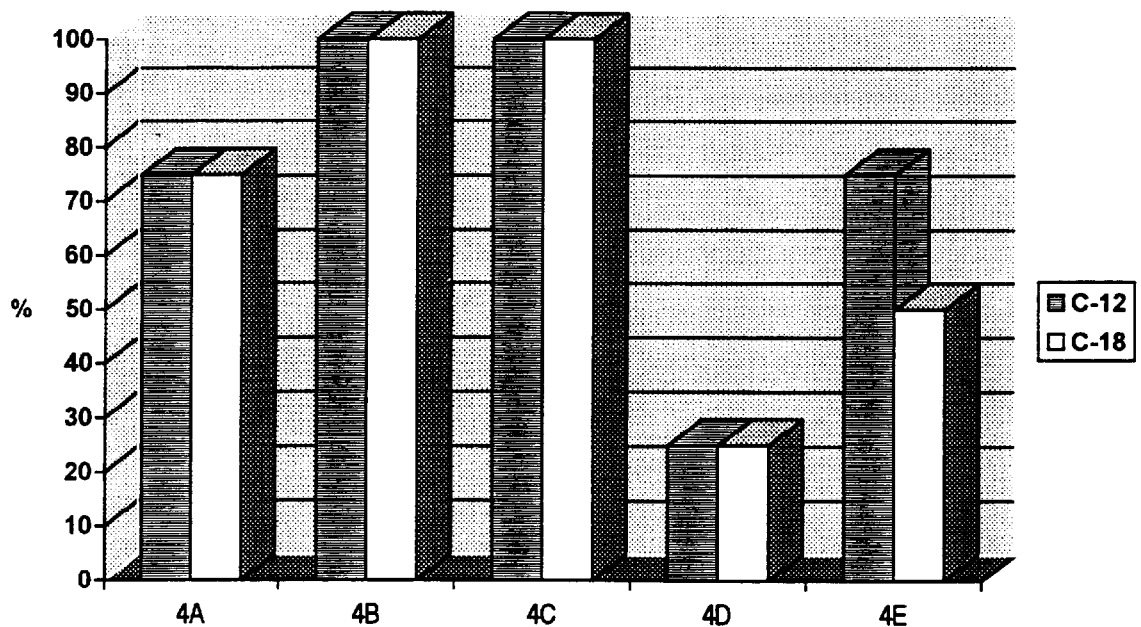
Figure 4 - hydroxybenzenes

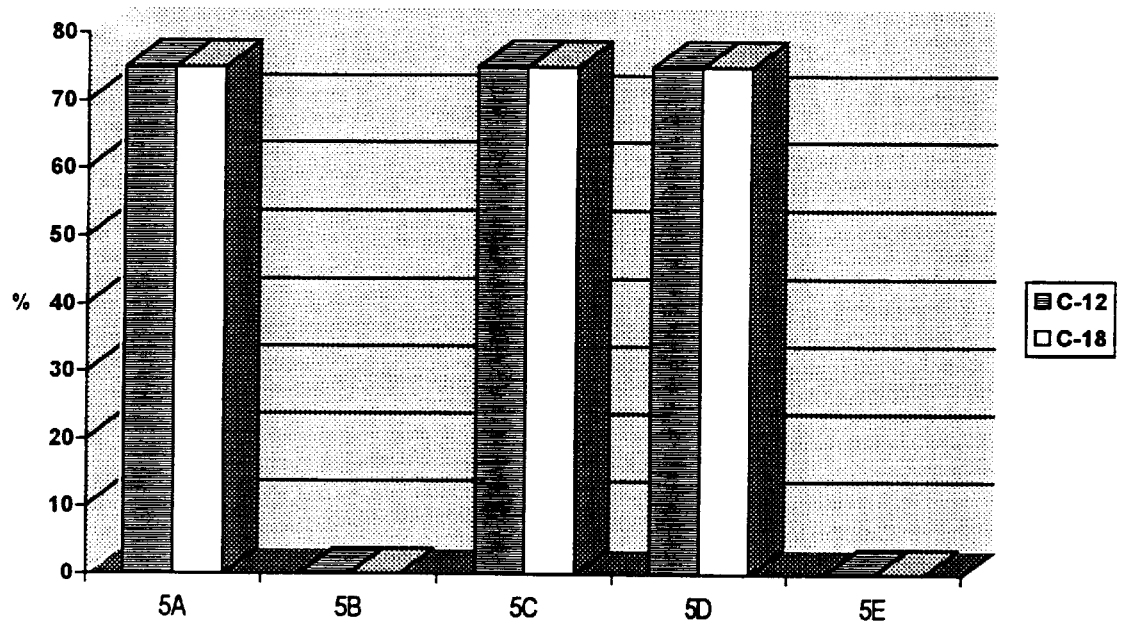
Figure 5 - aminobenzenes

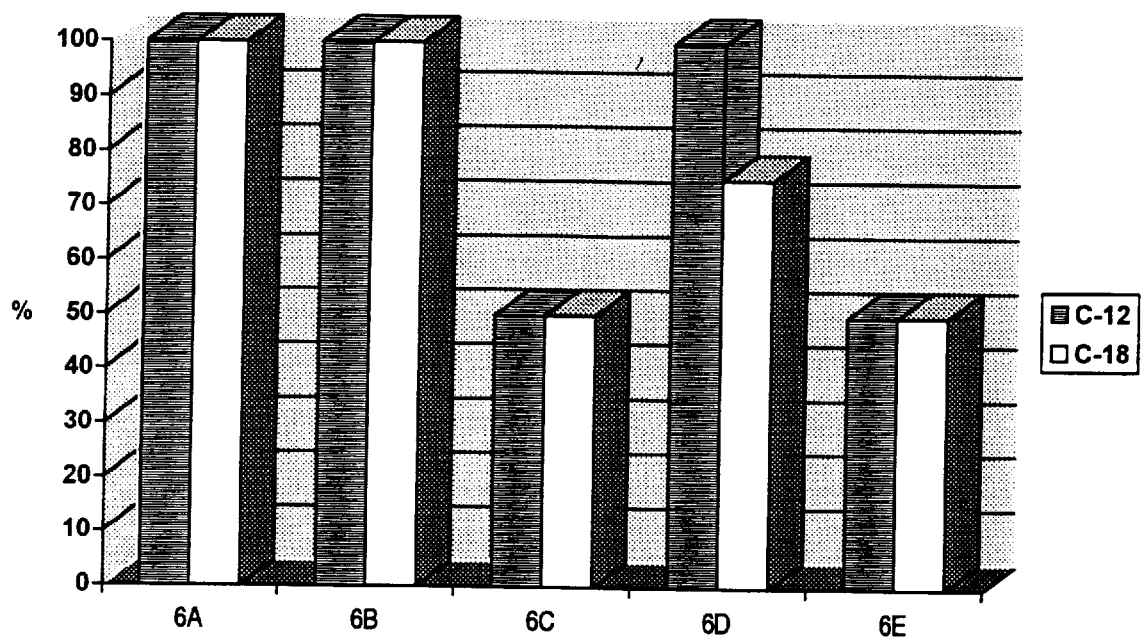
Figure 6 - nitrobenzenes

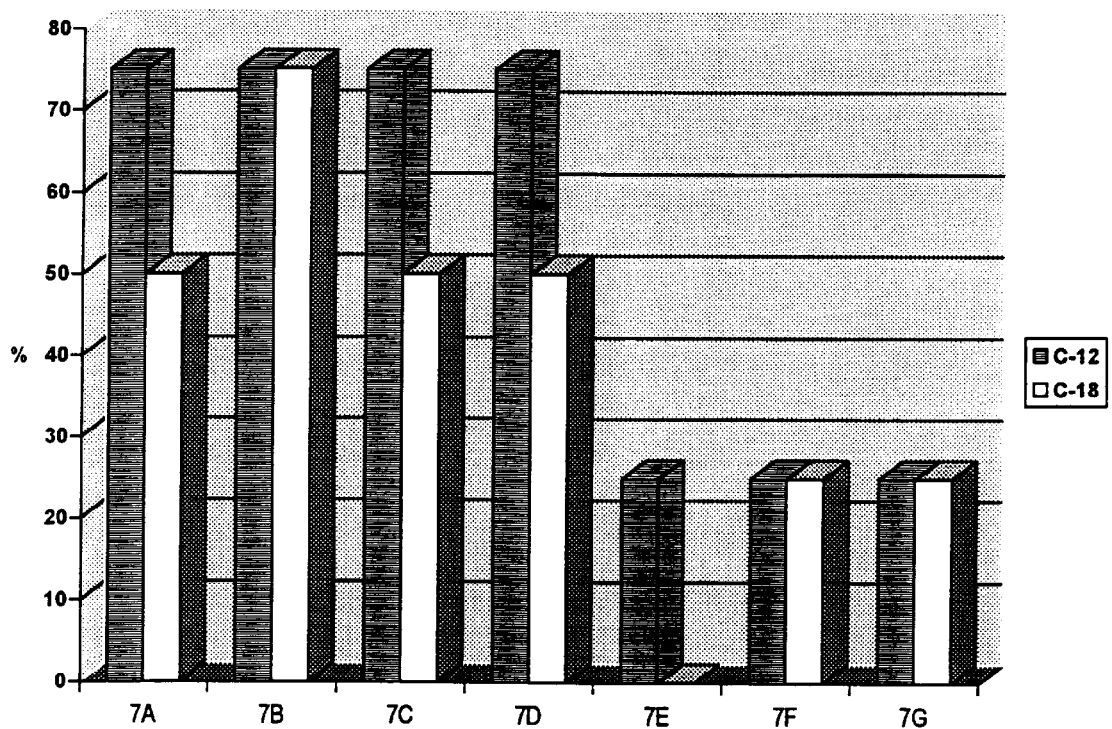
Figure 7- carboxylic acids

METHOD OF RENDERING ORGANIC COMPOUNDS SOLUBLE IN FATTY SYSTEMS, NOVEL CHEMICAL COMPLEXES OF SUCH COMPOUNDS AND VARIOUS APPLICATIONS OF THE COMPLEXES

This is a CPA of application Ser. No. 08/716,444, filed Sep. 16, 1996, which is a 371 of PCT/DR95/0008 filed Mar. 14, 1995. The most recent of these prior applications is hereby incorporated herein by reference, in its entirety.

The present invention relates to a method of rendering organic compounds containing hydrophilic groups soluble in fatty systems. The invention further relates to a group of novel chemical complexes formed in the method and to the use of these complexes for various purposes to be defined more specifically below.

More specifically the present invention concerns a method of making compounds containing hydrophilic groups more lipophilic, i.e. fat soluble. This is achieved due to the fact that according to the invention hydrophilic compounds form stable, fat soluble complexes with a lipophilic carrier.

Traditionally compounds are rendered fat soluble by derivatization, i.e. the compounds are modified chemically. This involves e.g. addition of an aliphatic side chain which is capable of rendering the compounds more lipophilic. In the textbook "Drug Formulation" (I. Racz, Chapter 4, John Wiley and Sons, 1989) esterification with a suitable fatty acid is mentioned as a method to make compounds more lipophilic. However, derivatization entails several problems. After the chemical modification the compounds often exhibit another degree of biological activity, whereby the desired activity may be lost. Further, the derivatization of a known harmless compound may lead to a new compound, the toxicity of which most be evaluated fundamentally, which is comprehensive and also expensive.

In the 1960's the discovery of liposomes called for attention. Liposomes consist of one or more concentric spheres of lipid bilayers surrounding aqueous compartments. Typically liposomes are used to encapsulate hydrophilic compounds in aqueous solution to obtain improved stability or biological uptake, i.e. in cosmetics. If liposomes are incorporated in a fatty phase, the hydrophilic compounds remain separated from the fatty phase, because in fact the hydrophilic compounds are present as a heterogeneous dispersion. Technically, and also with a view to the formulation of pharmaceuticals, the success of liposomes has been rather limited (see "Drug Targeting and Delivery", Chapter 6, edited by H. E. Junginger, Ellis Horwood 1992).

Liposomes do not represent an alternative to the present invention, since liposomes do not render the hydrophilic compounds lipophilic. The incorporation of compounds in liposomes may further give rise to problems and thus necessitate a derivatization of the compounds.

Complex formation is mentioned in the pharmaceutical literature, but only in connection with the improvement of the water solubility of the coupounds and as a problem related to sedimentation in certain combination pharmaceuticals.

A number of naturally occurring phenolic compounds, i.a. many flavones, flavone glycosides, phenolic di- and tri-terpenes, gingerols and other substances, exhibit a limited solubility in fatty as well as in aqueous systems. In spite of very interesting chemical and pharmacological properties many compounds, therefore, only find limited use as active agents in e.g. pharmaceuticals, foodstuffs and cosmetic products. Thus ginger (zingiber officinale) contains a number of 4-hydroxy-3-methoxyphenyl (HMP) compounds having interesting chemical and pharmacological effects, such as a potent antioxidant effect and a modulating effect on the functions of certain immune cells, which effects, however, are only sparsely exploitable due to the low solubility.

Spice plants of the labiatae family, such as sage, rosemary and thyme, contain phenolic diterpenes (Schwarz and Ternes, Z. Lebensmitteluntersuch. und Forsch. 195, 99 (1992) which can be extracted to yield an antioxidant with a strength comparable to that of the common antioxidant BHA (butylated hydroxyanisole). The above-mentioned phenolic compounds can be obtained from the resin by extraction of the oleoresins (mixture of ethereal oils and resins) of the plants. Traditionally, the oleoresins are extracted with an organic solvent, such as ethanol or methanol, which is subsequently distilled off. A more gentle way to extract the oleoresins is to use supercritical extraction with $CO_2$ (see U.S. Pat. No. 5,017,397 to Nguyen et al.).

Examples of HMP compounds extracted from ginger include 6-gingerol(5-hydroxy-1-(4-hydroxy-3-methoxyphenyl)-3-decanone) and 6-shogaol (1-(4-hydroxy-3-methoxyphenyl)-4-decen-3-one).

Not only the above, naturally occurring phenolic compounds, but many organic compounds in general containing hydrophilic groups are either totally insoluble or very sparsely soluble in fatty systems. Therefore, the valuable properties of such compounds quite often are not utilized.

Thus, it is the purpose of the present invention to render organic compounds containing hydrophilic groups, including the naturally occurring substances mentioned above, more soluble and, consequently, more accessible for a variety of uses. More specifically, it is the purpose of the invention to pack the organic compounds in a novel complex form using a carrier (a complexing agent) which:

(1) renders the organic compounds soluble in vegetable and animal fats of varying polarity;
(2) renders the organic compounds more biologically compatible, thus making it easier for the compounds to be absorbed in living organisms, and
(3) facilitates the incorporation of the organic compounds in pharmaceutical and cosmetic products and in various foodstuffs.

This is accomplished with the method according to the present invention in which organic compounds containing at least one hydrophilic group are rendered soluble in fatty systems, the method being characterized by the formation of a chemical complex between the organic compound and a certain carrier. It has surprisingly been found that a group of fatty acid esters of polyhydric hydroxyalkanes are particularly well suited as carriers for the purpose of the invention, said esters having the general formula:

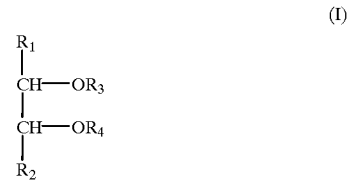

(I)

wherein $R_1$ is H or $-CH_2OR_5$, $R_2$ is H or $-CH_2OR_6$, and each of $R_3$, $R_4$, $R_5$ and $R_6$ is independently a saturated or unsaturated fatty acid moiety having 1–30 carbon atoms or a saturated fatty acid moiety having 1–3 carbon atoms, with the proviso that at least one of $R_3$, $R_4$, $R_5$ and $R_6$ is a saturated or unsaturated fatty acid moiety having 1–30 carbon atoms, and at least one or, when any of $R_1$ and $R_2$ is not H, at least two of $R_3$, $R_4$, $R_5$ and $R_6$ is a saturated fatty acid moiety having 1–3 carbon atoms.

A preferred group of such esters are fatty acid esters of glycerol having the general formula

(II)

wherein one of $R_7$, $R_2$ or $R_3$ represents a saturated or unsaturated fatty acid moiety of 4–30, especially 10–22 carbon atoms, and two of $R_8$, $R_2$ or $R_9$ represent a saturated fatty acid moiety of 1–3 carbon atoms.

FIG. 4 is a graphic illustration of the results of complex formation with several hydroxy compounds.

FIG. 5 is a graphic illustration of the results of complex formation with several amino compounds.

FIG. 6 is a graphic illustration of the results of complex formation with several nitro compounds.

FIG. 7 is a graphic illustration of the results of complex formation with several carboxylic acid compounds.

Figure 1:
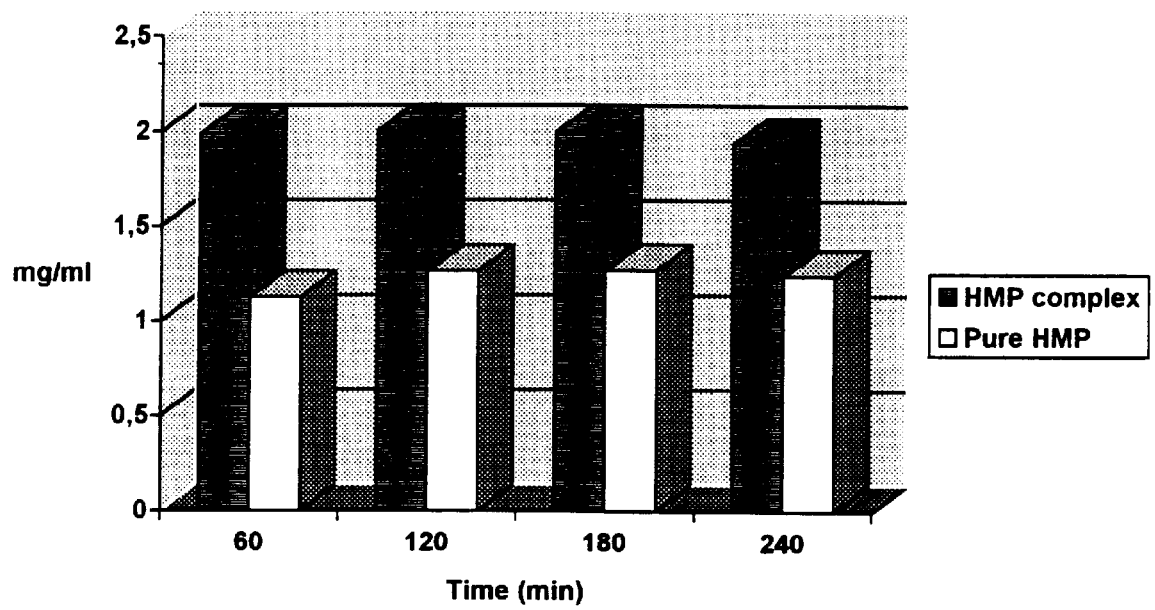
FIG. 1 is a graphic illustration of the results of a test for the availability of HMP using a composition comprising a complex of the invention.

The organic compounds to be complexed by the above carriers contain one or more functional groups preferably selected among hydroxy (—OH), amino (—$NH_2$), mono- and disubstituted amino (—NHR and —$NR_2$), carboxy (—COOH), nitro (—$NO_2$), mercapto (—SH), oxo (=O), imino (=NH), cyano (=N) and amido (—$CONH_2$). Also more lipophilic compounds having one or more hydrophilic groups such as vitamin E (tocopherols), vitamin A (retinols) and coenzyme $Q_{10}$ may be complexed by these carriers.

As mentioned above, the compound to be associated to the carriers may be selected among a wide variety of organic compounds. Some phenolic compounds are of particular interest, and among these the following substances should be mentioned:

(a) 4-hydroxy-3-methoxyphenyl compounds, e.g. gingerols and shogaols from ginger and curcuminoids from Curcuma longa;

(b) phenolic acids and derivatives thereof from herbs or other natural sources;

(c) flavonoid fractions of propolis, herbs or other natural sources.

Investigations have shown that complexes of the invention, especially acetic acid esters (I) coupled to the above substances (a)–(c), are stable, even at extreme pH values. Furthermore these complexes are readily soluble in various fatty substances despite the fact that prior to the complex formation the phenolic compounds were practically insoluble in the same fatty substances.

The applicant puts forward the hypothesis that the surprisingly effective and stable complex formation according to the invention resides in a non-covalent interaction (dipole—dipole) between the adjacent hydroxy-methoxy groups on the HMP compound and the nucleophilic oxygen atoms in connection with the acetic acid radicals of the carrier. The last mentioned nucleophilic regions are available for complex formation as a result of the short chain length of the acetic acid radicals. This is why a complex formation like this does not occur with triglycerides of medium or long chain fatty acids. On this background it is suggested that acetylated monoglycerides generally are able to form fat soluble complexes with any compound containing hydrophilic groups which can interact with the available nucleophilic region of the carrier.

The above esters (I) are capable of forming complexes with a wide range of organic compounds. These complexes are soluble and stable in various fats, even in rather high concentrations, which will be outlined in more detail in the experimental section below. This particular property of the complexes according to the invention gives rise to a number of potential applications.

Antioxidants and colorants for foodstuffs

Antioxidants are used in foodstuffs to prevent rancidity. A number of phenols extracted from herbs, e.g. carnosol, rosmanol and certain flavonoids and phenolic acids, are effective antioxidants. However, their use in foodstuffs is inhibited by a very low solubility in fats.

When these antioxidants form complexes with the esters (I) their solubility in fatty substances will increase markedly, and consequently they represent antioxidants of high effectiveness to preserve foodstuffs. A known food antioxidant, dl-α-tocopherol, which is widely used for the preservation of foodstuffs was compared with a complex of the invention containing HMP compounds from ginger with respect to antioxidant efficacy related to linolic acid oxidation at 37° C. over 30 hours. The antioxidant efficacy of the complex according to the invention was substantially higher than that of a corresponding amount of dl-α-tocopherol. These results lead to the assumption that the complex formation of the invention will also be applicable as regards phenolic food colorants from herbs, where efficient colorants, such as flavonoids and curcuminoids, at present only find limited use because the solubility and the dispersability are low.

Active compounds for use in diet supplements and peroral drugs

A large number of the above-mentioned hardly soluble compounds from herbs possess interesting pharmacological properties, i.a. antiinflammatory effects, including an antioxidant effect. It is, however, a major problem that these compounds are poorly absorbed via the alimentary tract, because it is a precondition for absorption that the compounds are available in solution. It now appears that a complex formation with an ester (I) according to the invention presents a solution to this problem. Thus it has been shown that the complexes of the invention fulfil the fundamental conditions for a satisfactory uptake:

(1) the complexes form micelles in the presence of bile acid salts;

(2) the complexes are miscible/compatible with the fatty substances which are present in the alimentary tract;

(3) by in vitro simulation the complexes were found to be stable in the environment typical for the decisive first part of the alimentary tract.

It is therefore most likely that the complexes will enter into micelles with a resultant minimum excretion of the active compounds. The active compounds will pass from the micelles into the intestine wall by diffusion.

In relation to peroral drugs the following uses of the complex formation are envisaged:

(1) Complex formation with pure substances, e.g. for pharmaceuticals. This has been done successfully with a number of different compounds, e.g. pure flavones, flavonols, curcuminoids, coenzyme $Q_{10}$, a-tocopherol.

(2) Complex formation with whole plant extracts for diet additives or natural medicine. This has been done successfully with extracts of propolis and extracts of widely different plant materials, e.g. ginger, turmeric, ginkgo biloba, ginseng, capsicum, rosemary, sage and oregano.

Active compounds for use in cosmetics

In the last decade antioxidants have found widespread use in cosmetic products because they interrupt the degenerative oxidation processes induced by exposure to the sun.

Complexes of natural antioxidants (e.g. gingerols) and carriers in the form of esters of formula (I) are evident candidates for use as active compounds in skin care products. It is a condition for the uptake of a compound through the skin that the compound can penetrate the fat barrier of the skin. The complexes of the invention have been shown to be fully compatible with fats like those of the skin.

Special formulation of pharmaceuticals

The complexes according to the invention may be used as pharmaceuticals regardless of the particular formulation and route of administration. This is due to the fact that the complexes of the invention are more biologically compatible than the compounds that can be complexed according to the invention. An example of this is the development of percutaneous pharmaceuticals, i.e. drugs to be absorbed through the skin. Complex formation according to the invention is believed to increase the applicability of drugs for transdermal delivery.

Technochemical applications

In addition to the uses described above the complexes according to the invention may find use for various technochemical purposes, e.g. as dyes, antioxidants or other additives for paint, plastics, petroleum products etc. The main advantage of the complexes is (as in the other applications) that a derivatization is avoided, a good compatibility with fats being necessary in connection with the use of various compounds for many technical purposes.

Stable soluble complexes with the yellow colorant curcumin have thus been formed successfully, curcumin as such being only weakly soluble in fatty systems. The complex, in contrast, turned out to be fully soluble in several types of fats.

The invention is illustrated further in the following experimental section.

EXPERIMENTAL SECTION

EXAMPLE 1

A. Complex Formation and Evaluation

The purpose of the following study was to test the formation, stability and fat compatibility of relevant complexes according to the invention.

Preparation of complexes 5 g of test compound either pure or in ethanolic solution was mixed with 20 g of each of the below mentioned carriers. After vigorously mixing ethanol was removed by evaporation.

As the carrier two diacetylated monoglycerides were used:
1. Diacetylated monoglyceride (hereafter C-12) with the following fatty acid composition on the monoglyceride: about 50% lauric acid (12:0), 20% myristic acid (14:0), 15% caprylic/capric acid (8:0 and 10:0) and 10% palmitic acid (16:0).
2. Diacetylated monoglyceride (hereafter C-18) with the following fatty acid composition on the monoglyceride: 80 % oleic acid (18:1) and 10% stearic acid (18:0).

The complex formation was performed using the following test compounds:

A concentrate of HMP compounds from ginger, derived from chinese ginger.

A concentrate of the phenolic fraction of propolis (PFP) with a high content of flavonoids.

An extract of ginkgo biloba with a high content of flavone glycosides and terpene lactones.

An extract of turmeric with a high content of curcumin.

An extract of capsicum with a high content of capsaicin.

Pure coenzyme $Q_{10}$.

The complex formation was successful according to the following examinations:
1. After the complex formation the samples were centrifuged at 800 G for 15 minutes. By microscopy (400–900× magnification with phase contrast) only a minor degree of sedimentation was observed.
2. The complex was hereafter evaluated by chromatography (TLC and reversed phase HPLC), and the complex formation was confirmed by a quantitative solubilization of the test compounds Stability in relation to PH-value The stability of the complex in a neutral, acidic and basic environment was tested as follows:
1. To 50 ml of a 0.2 M HCl solution 0.5 g of complex was added with magnetic stirring. After 15 and 120 minutes the stability and degree of dispersion of the complex was evaluated.
2. To 50 ml of a 0.2 M NaOH solution 0.5 g of complex was added with magnetic stirring. After 15 and 120 minutes the stability and degree of dispersion of the complex was evaluated.
3. To 50 ml of water (milli-Q) 0.5 g of complex was added with magnetic stirring. After 15 and 120 minutes the stability and degree of dispersion of the complex was evaluated.

All the above tested complexes were found to be stable in both neutral, acidic and basic environments.

Solubility in different fatty systems

The fatty compatibility of the complexes was evaluated as follows.

0.100 g of complex was mixed with 0.900 g of the following fatty substances:
1. Peanut oil ("Aextreff CT", Aarhus Oliefabrik A/S).
2. Caprylic and capric esters of propylene glycol.
3. Cetearyl octanoate.
4. Liquid paraffin.

After vigorous shaking the solubility of the complexes was inspected visually assisted by microscopy (900× magnification with phase contrast) after centrifugation at 1500 G for 15 minutes.

All the test compounds had a very limited solubility in the tested fatty systems before complex formation. In all the tested fatty systems complex formation resulted in a markedly improved solubility, whereas the obtained solubility was total in long chain triglyceride and caprylic/capric esters of propylene glycol and good with a marginal tendency to particle formation in cetearyl octanoate and liquid paraffin.

B. Simulation of Bioavailability

Many compounds have a limited bioavailability due to a poor solubility or dispersability in the gut. The purpose of the following investigation was to determine whether formation of complexes according to the invention results in an improved availability for absorption of the test compounds in the digestive system.

Preparation of complexes 5 g of test compound either pure or in ethanolic solution was mixed with 5–20 g of the below mentioned carrier. After vigorously mixing ethanol was removed by evaporation.

The following carrier was used: diacetylated monoglyceride with the following fatty acid composition based on the monoglyceride: about 50% lauric acid (12:0), 20% myristic acid (14:0), 15% caprylic/capric acid (8:0 and 10:0) and 10% palmitic acid (16:0).

The following test compounds were used:
A concentrate of HMP compounds from ginger (hereafter HMP), derived from chinese ginger.
A concentrate of the phenolic fraction of propolis (hereafter PFP) with a high content of flavonoids.
Pure coenzyme $Q_{10}$ (hereafter $Q_{10}$).

Simulation of the gut

Standardised enteric juice was prepared by mixing the following: 2.00 g of bile extract (B-8631, Sigma Chemical Company, St. Louis Mo., USA), 0.14 g pancreatin (P-1750 Sigma Chemical Company, St. Louis Mo., USA), 3.00 g sodium bicarbonate (E. Merck, Darmstadt, Germany) and 200 ml water (Milli-Q). The pH was adjusted to 8.3.

0.500 g complex and 50 ml of standardised enteric juice was mixed in a 100 ml vessel and placed on a shaking water bath at 37 degrees Celsius under moderate agitation. As controls pure test compound corresponding to 0.500 g complex was used instead of 0.500 g complex.

Samples of 1.000 ml were collected after 60, 120, 180 and 240 minutes. The samples were extracted with 1.5 ml of 1-butanol. The concentration of test compound in the enteric juice was determined by an appropriate method (spectrophotometrically or by HPLC).

Results

Figure 2:
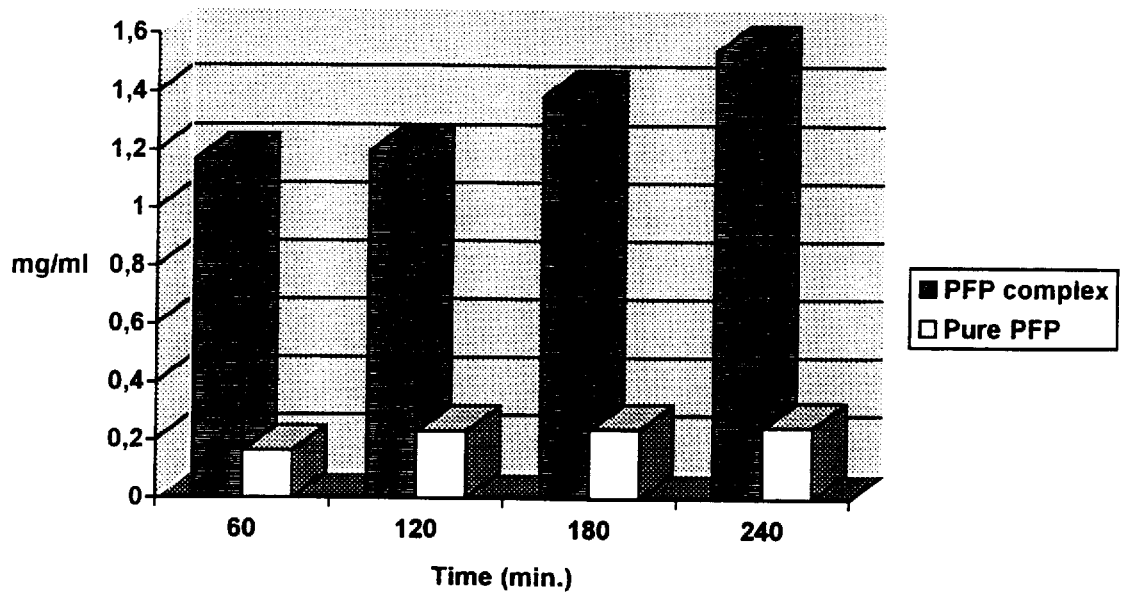
FIG. 2 is a graphic illustration of the results of a test for the availability of PFP using a composition comprising a complex of the invention.
Figure 3:
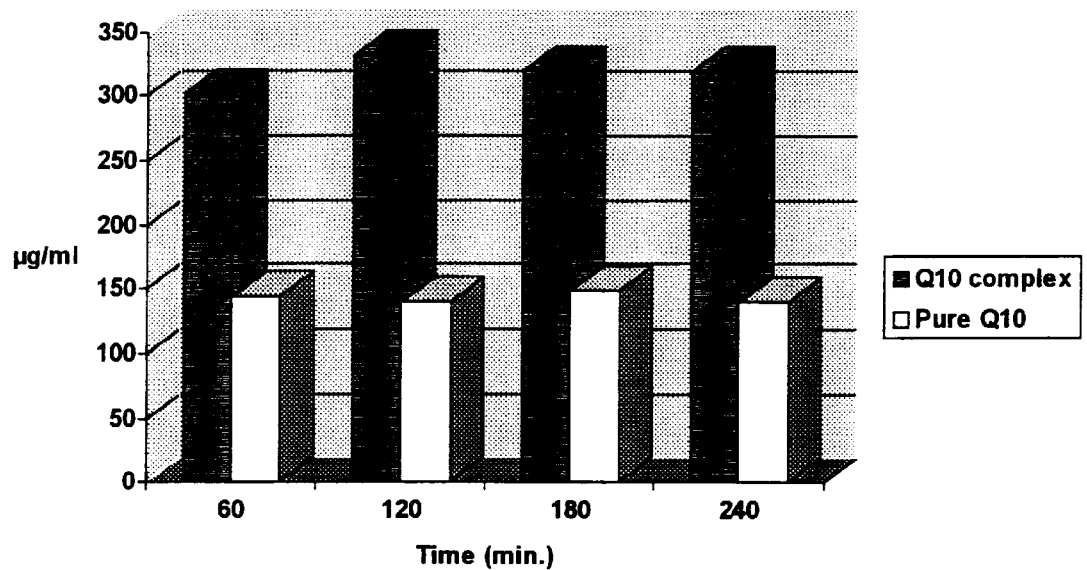
FIG. 3 is a graphic illustration of the results of a test for the availability of $Q_{10}$ using a composition comprising a complex of the invention.

The results are presented in FIGS. 1–3, where the concentration of test compound in the enteric juice at a given time is shown (mean of two experiments).

The results concerning HMP are shown in FIG. 1. The availability of HMP was overall 1,6 times as high in the complex form compared to pure HMP (mean over the entire experiment).

The results concerning PFP are shown in FIG. 2. The availability of PFP was overall 5,6 times as high in the complex form compared to pure PFP (mean over the entire experiment).

The results concerning $Q_{10}$ are shown in FIG. 3. The availability of $Q_{10}$ was overall 2,2 times as high in the complex form compared to pure $Q_{10}$ (mean over the entire experiment).

Consequently the complex formation resulted in a strongly improved availability of the active compounds over the entire experimental period indicating a significantly improved bioavailability.

In an experiment similar to the present one several traditional carriers for pharmaceuticals were tested against the carrier of the invention. It was thus found that e.g. long and medium chain triglycerides and polyoxyethylene sorbitan monooleate ("Polysorbate 80") only resulted in a very limited improvement of the availability of the test compounds and consequently did not represent an alternative to the present invention.

EXAMPLE 2

In the following study the ability of the carrier according to the invention to form complexes with organic compounds containing various functional groups was investigated. More specifically the complex formation of the carrier with aromatic hydroxy, amino, nitro and carboxylic acid derivatives was studied.

Preparation of complexes 50.0 mg test compound was mixed with 450.0 mg carrier and the mixture was placed on a boiling water bath for 30 minutes. The mixture was shaken vigorously every 10 minutes.

As the carrier two types of acetylated monoglyceride were used:
1. Diacetylated monoglyceride (hereafter C-18) with the following fatty acid composition on the monoglyceride: about 80% oleic acid (18:1) and 10% stearic acid (18:0).
2. Diacetylated monoglyceride (hereafter C-12) with the following fatty acid composition on the monoglyceride: about 50% lauric acid (12:0), 20% myristic acid (14:0), 15% caprylic/capric acid (8:0 and 10:0) and 10% palmitic acid (16:0).

The complex formation was tested using the following test compounds:
1,2,3-trihydroxybenzene
1,2-dihydroxybenzene
1,3-dihydroxybenzene
1,4-dihydroxybenzene
1,2-diaminobenzene
1,4-diaminobenzene
3-nitrophenol
4-nitrophenol
4-methoxyphenol
4-aminophenol
2-amino-4-nitrophenol
4-amino-2-nitrophenol
2-nitroaniline
3-nitroaniline
4-nitroaniline
2,4-diaminotoluene
2,6-diaminotoluene
2-aminobenzoic acid
2-nitrobenzoic acid
3-nitrobenzoic acid
4-nitrobenzoic acid
2-hydroxybenzoic acid
3-hydroxybenzoic acid
3,4-dihydroxybenzoic acid
Curcumin Evaluation of the complex formation
1) After the complex formation the samples were cooled and centrifuged at 800 G for 15 minutes.
2) It was determined by microscopy (400–900× magnification with phase contrast) whether there were any visible particles.
3) 100 mg Complex was dissolved in 400 mg peanut oil ("Aextreff CT", Aarhus Oliefabrik A/S) in which the test compounds, with a few exceptions, were insoluble. It was ascertained by microscopy (400–900× magnification with phase contrast) that no precipitation of test compound occurred.
4) The complexed test compounds were recovered by TLC and HPLC.

Results

The results of the complex formation with the test compounds are shown in FIGS. 4–7. The figures show how many percents of the test compound have been complexed with the two carriers (C-12 and C-18).

a) The results of complexing with various hydroxy compounds appear from FIG. 4. The following hydroxy compounds were tested:
4A: 1,2,3-trihydroxy-benzene
4B: 1,2-dihydroxy-benzene
4C: 1,3-dihydroxy-benzene
4D: 1,4-dihydroxy-benzene
4E: Curcumin.
b) The results of complexing with amino compounds appear from FIG. 5. The following amino compounds were tested:

5A: 1,2-diamino-benzene
5B: 1,4-diamino-benzene
5C: 2,6-diamino-toluene
5D: 2,4-diamino-toluene
5E: 4-amino-phenol.
c) The results of complexing with nitro compounds appear from FIG. 6. The following nitro compounds were tested:
6A: 3-nitro-phenol
6B: 4-nitro-phenol
6C: 4-nitro-aniline
6D: 3-nitro-aniline
6E: 2-nitro-aniline.
d) The results of complexing with various carboxylic acids appear from FIG. 7. The following carboxylic acids were tested:
7A: 2-amino-benzoic acid
7B: 2-nitro-benzoic acid
7C: 3-nitro-benzoic acid
7D: 4-nitro-benzoic acid
7E: 2-hydroxy-benzoic acid
7F: 3-hydroxy-benzoic acid
7G: 3,4-dihydroxy-benzoic acid.

Thus, we have successfully tested complex formation according to the invention on a broad range of aromatic compounds. It has been possible to form stable complexes between two carriers comprised by formula (I) and a variety of hydroxy, amino and nitro compounds as well as carboxylic acids.

In most cases complex formation occurred with a yield of from 25% up to 100%. Complex formation was possible with compounds having one or more hydrophilic groups in different positions.

In certain instances carrier C-12 was superior to carrier C-18. Hence, it is likely that an optimal carrier can be developed for specific compounds, e.g. compounds for which a poor complex formation is observed in the present experiment.

Altogether the results demonstrate the broad applicability of the present invention.

I claim:

1. A method of rendering organic compounds containing at least one hydrophilic group soluble in fatty systems, said method comprising forming a chemical complex between the organic compound and a carrier selected from the group consisting of fatty acid esters of polyhydric hydroxyalkanes having the general formula

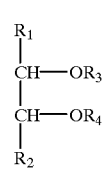

(I)

wherein $R_1$ is H or $-CH_2OR_5$, $R_2$ is H or $-CH_2OR_6$, and each of $R_3$, $R_4$, $R_5$ and $R_6$ is independently a saturated or unsaturated fatty acid moiety having from 4 to 30 carbon atoms or a saturated fatty acid moiety having from 1 to 3 carbon atoms, with the proviso that at least one of $R_3$, $R_4$, $R_5$, and $R_6$ is a saturated or unsaturated fatty acid moiety having from 4 to 30 carbon atoms, and at least one or, when any of $R_1$ and $R_2$ is not H, at least two of $R_3$, $R_4$, $R_5$ and $R_6$ is a saturated acid moiety having from 1 to 3 carbon atoms.

2. A method according to claim 1 wherein the carrier is selected from the group consisting of fatty acid esters of glycerol having the general formula

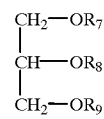

(II)

wherein one of $R_7$, $R_8$ or Rg represents a saturated or unsaturated acid moiety having from 4 to 30 carbon atoms, and two of $R_7$, $R_8$ or $R_9$ represent a saturated fatty acid moiety having from 1 to 3 carbon atoms.

3. A method according to claim 1 wherein said organic compound containing at least one hydrophilic group contains one or more functional groups selected from the group consisting of hydroxy, amino, monosubstituted amino, disubstituted amino, carboxy, nitro, mercapto, oxo, imino, cyano and amido.

4. A method according to claim 1 wherein said organic compound containing at least one hydrophilic group is a phenolic compound, selected from the group consisting of 4-hydroxy-3-methoxyphenyl compounds, phenolic diterpenes, flavonoid fractions and other phenolic fractions extracted from herbs, selected from the group consisting of ginger, ginkgo biloba, turmeric, capsicum, ginseng, sage, rosemary, and propolis.

5. A method according to claim 1 wherein the saturated acid moiety having from 1 to 3 carbon atoms is acetate.

6. A composition comprising chemical complex between an organic compound containing at least one hydrophilic group and a carrier selected from the group consisting of fatty acid esters of polyhydric hydroxyalkanes having the general formula

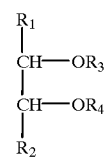

(I)

wherein $R_1$ is H or $-CH_2OR_5$, $R_2$ is H or $-CH_2OR_6$, and each of $R_3$, $R_4$, $R_5$ and $R_6$ is independently a saturated or unsaturated fatty acid moiety having from 4 to 30 carbon atoms or a saturated acid moiety having from 4 to 30 carbon atoms or a saturated fatty acid moiety having from 1 to 3 carbon atoms, with the proviso that at least one of $R_3$, $R_4$, $R_5$ and $R_6$ is a saturated or unsaturated fatty acid moiety having from 4 to 30 carbon atoms, and at least one or, when any of $R_1$ and $R_2$ is not H, at least two of $R_3$, $R_4$, $R_5$ and $R_6$ are a saturated acid moiety having from 1 to 3 carbon atoms.

7. A composition according to claim 6, wherein the carrier is selected from the group consisting of fatty acid esters of glycerol having the general formula

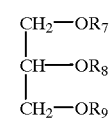

wherein one of $R_7$, $R_8$, $R_9$ represents a saturated or unsaturated acid moiety of having from 4 to 30 carbon atoms, and two of $R_7$, $R_8$ or $R_9$ represent a saturated fatty acid moiety having from 1 to 3 carbon atoms.

8. A composition according to claim 6, wherein said organic compound containing at least one hydrophilic group contains one or more functional groups selected from the group consisting of hydroxy, amino, monosubstituted amino, disubstituted amino, carboxy, nitro, mercapto, oxo, imino, cyano and amido.

9. A composition according to claim 6, wherein said organic compound containing at least one hydrophilic group is a phenolic compound, preferably selected from the group consisting of 4-hydroxy-3-methoxyphenyl compounds, phenolic diterpenes, flavonoid fractions and other phenolic fractions extracted from herbs, selected from the group consisting from ginger, ginkgo biloba, turmeric, capsicum, ginseng, sage, rosemary, and propolis.

10. A composition according to claim 6, wherein the saturated acid moiety having from 1 to 3 carbon atoms is acetate.

11. A pharmaceutical composition comprising a composition according to claim 6.

12. A cosmetic composition comprising a composition according to claim 6.

13. A foodstuff or feed comprising a composition according to claim 6.

14. A diet supplement or natural medicine comprising a composition according to claim 6.

15. A technochemical composition comprising a composition according to claim 6.

16. A method according to claim 2, wherein one of $R_7$, $R_8$ or $R_9$ represents a saturated or unsaturated fatty acid moiety having from 10 to 22 carbons.

17. A composition according to claim 7, wherein one of $R_7$, $R_8$ or $R_9$ represents a saturated or unsaturated fatty acid moiety having from 10 to 22 carbon atoms.

18. A method for the preparation of a pharmaceutical composition, said method comprising:

mixing a complex according to claim 6 with a pharmaceutically acceptable carrier or diluent.

* * * * *